United States Patent
Giard et al.

(10) Patent No.: US 8,487,120 B2
(45) Date of Patent: Jul. 16, 2013

(54) PROCESSES FOR PRODUCING 3-(METHYLTHIO) THIOPHENE

(75) Inventors: Thierry Giard, Wavre (BE); Vincent L. Mutterer, Bousval (BE); Christophe Durvaux, Brussels (BE)

(73) Assignee: Albemarle Corporation, Baton Rouge, LA (US)

( * ) Notice: Subject to any disclaimer, the term of this patent is extended or adjusted under 35 U.S.C. 154(b) by 0 days.

(21) Appl. No.: 13/394,462

(22) PCT Filed: Sep. 16, 2010

(86) PCT No.: PCT/US2010/049105
§ 371 (c)(1),
(2), (4) Date: Mar. 6, 2012

(87) PCT Pub. No.: WO2011/041126
PCT Pub. Date: Apr. 7, 2011

(65) Prior Publication Data
US 2012/0178943 A1 Jul. 12, 2012

Related U.S. Application Data

(60) Provisional application No. 61/246,693, filed on Sep. 29, 2009.

(51) Int. Cl.
*C07D 333/34* (2006.01)
(52) U.S. Cl.
USPC ......................................................... 549/62
(58) Field of Classification Search
USPC ......................................................... 549/62
See application file for complete search history.

(56) References Cited

PUBLICATIONS

Wu, X., et al. "Room Temperature Stable 3-Lithiothiophene: a Facile Synthesis of 3-Functional Thiophenes." Tetrahedron Letters. vol. 35, No. 22, (1994), pp. 3673-3674.*

Rieke, R.D., et al. "Synthesis of Regioregular Head-to-Tail Poly[3-(alkylthio)thiophenes]. A Highly Electroconductive Polymer." Macromolecules. vol. 28, (1995), pp. 2101-2102.*

Folli, et al; "Synthesis of 3,3'-and 4,4'-Bis(alkylsulfanyl)-2,2'-bithiophenes from the Corresponding Diobromo Derivatives Through Lithiation"; Journal of Chemical Research; No. 2, pp. 552-569; Jan. 1, 1996.

Wu, et al; "Room Temperature Stable 3-lithiothiophene: A Facile Synthesis of 3-functional Thiophenes"; Tetrahedron Letters; vol. 35, No. 22, pp. 3673-3674; Jan. 1, 1994.

Holland, et al; "Biotransformation of Organic Sulfides. Part 12. Conversion of Heterocyclic Sulfides to Chiral Sulfoxides by *Heminthosporium* sp. NRRL 4671 and *Mortierella isabellina* ATCC 42613"; Can. J. Chem.; vol. 77, No. 4; pp. 463-471; Jan. 1, 1999.

* cited by examiner

*Primary Examiner* — Andrew Kosar
*Assistant Examiner* — John S Kenyon
(74) *Attorney, Agent, or Firm* — Marcy M. Hoefling; Jeremy J. Kliebert; James A. Jubinsky

(57) ABSTRACT

Processes are provided for producing 3-(methylthio) thiophene by (i) combining at least an alkyl lithium, one or more alkanes and an ether to form a first combination, (ii) at a temperature of about −30° C. to about −25° C. and over a time period of at least about 30 minutes, adding 3-bromothiophene diluted in an ether to the first combination to form a second combination, (iii) at a temperature of about −25° C. to about −20° C. combining at least the second combination and dimethyl disulfide, and (iv) yielding at least the 3-(methylthio)thiophene.

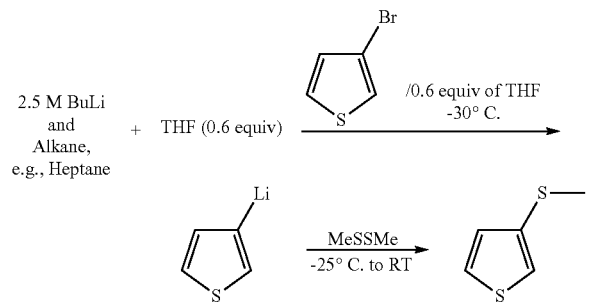

7 Claims, No Drawings

PROCESSES FOR PRODUCING 3-(METHYLTHIO) THIOPHENE

BACKGROUND 3-(Methylthio)thiophene is used in the electronic industry, e.g., 3-(Methylthio)thiophene can be used as intermediate for the synthesis of API (see for example WO2005040110). It is also used for yielding oligothiophene (J. Org. Chem. 1996, 61, 8285 and ref herein), oligomers that have attracted great attention for their chemical stability, ease of fictionalization, and variety of useful properties.

The synthesis of this compound has already been described (see for example, Tetrahedron Letters 1994, Vol. 35, No. 22, pp. 3673-3674 and WO 2005/040110). When tetrahydrofuran ("THF") is used as the solvent, the described process usually involves the mixing of 3-bromothiophene and butyl lithium at −40° C. in hexane. THF is added to allow the formation of 3-lithiothiophene via metal halogen exchange that yields 3-lithio thiophene at −40° C., followed by a reaction between 3-lithiothiophene and an electrophile at room temperature, e.g., about 20° C., Subsequently, dimethyl disulfide is added to obtain 3-(methylthio)thiophene, e.g., in 71% yield.

However, exothermicity that is inappropriate for most commercial applications is observed at −40° C. (+9° C. with a dry ice bath at −40° C.) upon the addition of THF.

Thus, there is a need for commercially suitable processes for production of 3-(methylthio)thiophene.

THE INVENTION

This invention meets the above-described needs by providing processes that comprise (i) combining at least an alkyl lithium, one or more alkanes, and a first ether to form a first combination, (ii) at a temperature of about −30° C. to about −25° C. and over a time period of at least about 30 minutes, adding 3-bromothiophene diluted in a second ether to the first combination to form a second combination, (iii) at a temperature of about −25° C. to about −20° C. combining at least the second combination and dimethyl disulfide, and (iv) yielding at least 3-(methylthio)thiophene. The first ether and second ether can be the same or different. For example, a process according to this invention can comprise (i) combining at least butyl lithium, one or more alkanes, and about 0.6 equiv of THF to form a first combination, (ii) at a temperature of about −30° C. to about −25° C. and over a time period of at least about 30 minutes, adding 3-bromothiophene diluted in a second ether to the first combination to form a second combination, (iii) at a temperature of about −25° C. to about −20° C. combining at least the second combination and dimethyl disulfide, and (iv) yielding at least 3-(methylthio)thiophene.

A practical and original process has been developed, which can be used, e.g., to synthesize 3-(methylthio)thiophene from 3-bromothiophene in 76% yield. The addition of 3-bromothiophene diluted in 0.6 equivalents of THF on a mixture of butyl lithium, hexane, heptane and 0.6 equivalents of THF at −30° C. leads to the formation of 3-lithiothiophene, which is subsequently reacted with dimethyl disulfide to yield 3-(methylthio)thiophene.

Processes according to this invention involve the progressive addition of 3-bromothiophene diluted in a suitable amount of a suitable (second) ether into a mixture of a suitable alkyl lithium with one or more suitable alkanes and another suitable (first) ether. The addition time can be at least about 30 minutes, and can be from at least about 30 minutes up to about 90 minutes. The first and second ethers can be the same or different. Suitable ethers include THF, MTBE, 2-methyl THF, methyl cyclopentyl ether, and the like. The amount of ether suitable for use in any particular process according to this invention can be determined by those skilled in the art given the teachings of this specification. For example, 0.6 equivalents of THF can be used as the first ether, and 0.6 equivalents of THF can be used as the second ether. Suitable alkyl lithiums include butyl lithium, hexyl lithium, and the like. Suitable alkanes include hexane, heptane, methyl cyclohexane, and the like. Butyl lithium is typically sold as a mixture in hexane. At −40° C. and with a dry ice bath at −40° C., we have detected no temperature increase during a process according to this invention (which mean that the exothermicity is much more manageable); and after addition of dimethyl disulfide, the level of 2-(methylthio)thiophene has consistently been observed to be below 0.5% area GC. We have also demonstrated the possibility to carry out this reaction at −30° C., −20° C. or even at 0° C. with nevertheless an impurity content a little bit higher (84.8% area GC (solvent excluded) of 3-(methylthio)thiophene at 0° C. vs. 93% (solvent excluded) at −30° C.). After distillation, highly pure compound have been obtained in non optimized −76% overall yield (>99% area GC), which could be improved by minimizing losses during the distillations step.

A process according to this invention can be illustrated by the following example schematic:

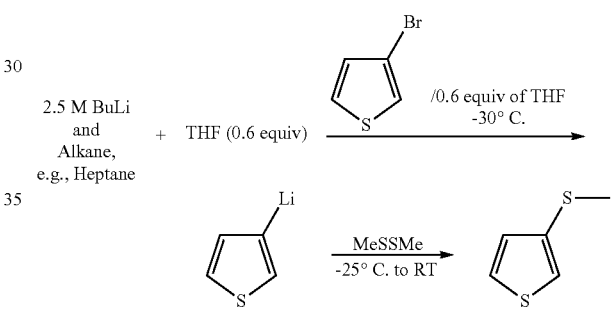

EXAMPLES

The following example is illustrative of the principles of this invention. It is understood that this invention is not limited to any one specific embodiment exemplified herein, whether in the examples or the remainder of this patent application.

Example 1

In an example of this invention, the following process was followed giving the results shown:

1. Heptane (214.5 ml) and 2.5 M butyl lithium (127 ml) were loaded into a flask.
2. The reaction (i.e., contents of the flask) was cooled to −30° C.
3. THF (11.3 g) was added to the flask.
4. A mixture of THF (11.3 g) and 3-bromothiophene (42.9 g) was prepared.
5. The THF/3-bromothiophene mixture was added to the reaction mixture in the flask between −25° C. and −30° C. over 30 min.
6. The reaction mixture was stirred for 1 h.
7. Dimethyl disulfide (29.76 g) was added over 45 min between −25° C. and −20° C.
8. The reaction mixture was stirred for 1 h.

9. The reaction mixture was heated up to 0° C.
10. Water (170 ml) was added to the reaction mixture and the reaction mixture was stirred for 30 min.
11. An organic phase up (a phase cut) was conducted.
12. Water (60 ml) was added to the reaction mixture and it was stirred for 15 min.
13. An organic phase up (a phase cut) was conducted.
14. THF solvent was distilled out at 40° C. under reduced pressure.
15. The desired product, 3-(methylthio)thiophene, was distilled out between 90 and 100° C. under 80 and 40 mbars.
16. 25.7 g of 3-(methyl)thiophene were obtained, giving a 76% yield.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

What is claimed is:

1. A process to produce 3-(methylthio)thiophene, comprising:
    combining at least an alkyl lithium, a first ether, and one or more alkanes to form a first combination,
    at a temperature of −30° C. to −25° C. and over a time period of at least about 30 minutes, adding 3-bromothiophene diluted in a second ether to the first combination to form a second combination, wherein the second ether can be the same as or different from the first ether,
    at a temperature of −25° C. to −20° C. combining at least the second combination and dimethyl disulfide,
    yielding at least the 3-(methylthio)thiophene.

2. A process according to claim 1 wherein the alkyl lithium comprises butyl lithium or hexyl lithium.

3. A process according to claim 1 wherein the one or more alkanes comprises hexane, heptane or methyl cyclohexane.

4. A process according to claim 1 wherein the first ether comprises THF, MTBE, 2-methyl THF, or methyl cyclopentyl ether, and the second ether comprises THF, MTBE, 2-methyl THF, or methyl cyclopentyl ether.

5. A process according to claim 1 wherein the first ether and the second ether are the same.

6. A process according to claim 1 wherein the first ether comprises THF and the second ether comprises THF.

7. A process to produce 3-(methylthio)thiophene, comprising:
    combining at least butyl lithium in hexane, heptane and 0.6 equivalents of tetrahydrofuran to form a first combination,
    at a temperature of −30° C. to −25° C. and over a time period of at least 30 minutes, adding 3-bromothiophene diluted in tetrahydrofuran to the first combination to form a second combination,
    at a temperature of −25° C. to −20° C. combining at least the second combination and dimethyl disulfide,
    yielding at least the 3-(methylthio)thiophene.

* * * * *